United States Patent [19]

Okorodudu

[11] Patent Number: 5,030,368

[45] Date of Patent: Jul. 9, 1991

[54] N,N-DIORGANODITHIOCARBAMATE DERIVATIVES AND LUBRICANT COMPOSITIONS CONTAINING SAME

[75] Inventor: Abraham O. M. Okorodudu, West Deptford, N.J.

[73] Assignee: Mobil Oil Corporation, Fairfax, Va.

[21] Appl. No.: 236,404

[22] Filed: Aug. 24, 1988

[51] Int. Cl.$^5$ .......................................... C10M 137/02
[52] U.S. Cl. ................................... 252/46.7; 558/130
[58] Field of Search ......................................... 558/130

[56] References Cited

U.S. PATENT DOCUMENTS

| | | | |
|---|---|---|---|
| 3,462,368 | 8/1969 | Wollensak et al. | 252/46.7 |
| 3,536,623 | 10/1970 | Hu et al. | 252/46.7 |
| 4,101,432 | 7/1978 | Okorodudu | 252/49.8 |
| 4,104,181 | 8/1978 | Landis et al. | 252/46.7 |
| 4,252,660 | 2/1981 | Okorodudu | 252/46.7 |
| 4,428,861 | 1/1984 | Bridger | 252/32.7 E |
| 4,609,480 | 9/1986 | Hata et al. | 252/47 |
| 4,648,985 | 5/1987 | Thorsell et al. | 252/32.5 |
| 4,758,362 | 7/1988 | Butke | 252/47 |

FOREIGN PATENT DOCUMENTS

| | | | |
|---|---|---|---|
| 527419 | 7/1956 | Canada | 558/130 |
| 4055523 | 5/1979 | Japan | 558/130 |

*Primary Examiner*—Prince E. Willis
*Assistant Examiner*—Jerry D. Johnson
*Attorney, Agent, or Firm*—A. J. McKillop; C. J. Speciale; M. J. Mlotkowski

[57] ABSTRACT

Disclosed are products derived from the reaction of amine or metal salts of N,N-diorganodithiocarbamic acids with organo phosphorus halides. These compositions are useful as antioxidants and antiwear additives in lubricating oil compositions.

6 Claims, No Drawings

N,N-DIORGANODITHIOCARBAMATE DERIVATIVES AND LUBRICANT COMPOSITIONS CONTAINING SAME

FIELD OF THE INVENTION

This invention relates to the novel compounds resulting when organo phosphorus halides are reacted with the amine or metal salts of N,N-diorganodithiocarbamic acids. In another aspect this invention relates to lubricant compositions containing these compounds.

DISCUSSION OF THE PRIOR ART

Metal salts of dithiocarbamic acid have been known as additives for lubricating oils. U.S. Pat. No. 4,226,733 discloses the use of nickel alkyldithiocarbamates as additives to prevent ultra-violet degradation of lube oils. U.S. Pat. No. 4,428,861 discloses sulfidation reactions of dialkyl dithiocarbamates. U.S. Pat. No. 4,351,759 discloses that 1,1'-dialkyl phosphites can be prepared by reacting an alkylated 2,2'biphenol with phosphorus trichloride in a solvent to give the corresponding phosphorochloridite which in turn is reacted with an alkyl metal, alcoholate or phenolate to yield a product which can be used as an additive in mineral and synthetic fluids such as lubricating oils.

SUMMARY OF THE INVENTION

In one aspect this invention comprises the reaction product resulting from the reaction of an organo phosphorodichloridite and an N,N-diorganodithiocarbamate. In another aspect this invention comprises the lubricant composition containing the afore-described reaction product and a lubricating oil.

DESCRIPTION OF THE INVENTION

Representative of the amine or metal dithiocarbamate salts are those having the following structure

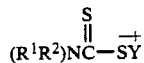

where $R^1$ and $R^2$ are the same or different. $R^1$ and $R^2$ are each a hydrocarbyl group containing from 1 to 36 carbon atoms, having none or at least one heteroatom which can be oxygen, sulfur, or nitrogen. $R^1$ and $R^2$ are selected from alkyl, alkenyl, aryl, aralkyl, alkaryl groups and can contain phenyl, naphthyl, or anthryl substituents; $R^1$, $R^2$ can be a $(CH_n)_m$ group comprising part of an alicyclic or heterocyclic system selected from, for example, pyrrole, pyrrolidine, piperidine, morpholine, etc., where n is 1 or 2 and m is 2 to 8. Y is an ammonium or metal radical.

A preferred dithiocarbamate salt is the triethylammonium salt of N,N-di-2-ethylhexyl-dithiocarbamic acid. This salt is prepared by reacting bis-2-ethylhexyl amine and carbon disulfide in the presence of triethylamine in toluene.

Other preferred metal or amine salts include the amine or metal salts of other diorganodithiocarbamic acids derived from other secondary amines, for example, dialkyl, aryl alkyl, diaryl, dialkylaryl, diarylalkyl, alkyl arylalkyl, arylalicyclic, or heterocyclic amines, reacted with carbon disulfide in the presence of suitable aprotic solvents such as toluene, benzene or hexane. Other suitable metals salts include the sodium or potassium salts of N,N-diorganodithiocarbamates prepared by reacting a secondary amine with carbon disulfide in the presence of sodium, or potassium hydroxide in toluene.

The organo phosphorodichloridite compounds have the structural formula:

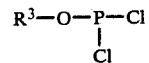

where $R^3$ is an aryl, alkaryl, aralkyl, or saturated or unsaturated alkyl substituent having none or at least one heteroatom which can be nitrogen, oxygen, or sulfur. The organo phosphorodichloridite compounds are prepared by reacting an aryl, or alkaryl phenol, a saturated or unsaturated alkyl alcohol, or other hydroxy-containing organic compound with a phosphorus trihalide (preferably phosphorus trichloride). Preferred hydroxy-bearing compounds include but not exclusively, 4-nonyl phenol, phenol, 2-ethylhexyl alcohol, butanol and oleyl alcohol.

The organo phosphorodichloridite compound and the ammonium or metal dithiocarbamate salt are reacted in a molar ratio of 1 mole of phosphorodichloridite compound to 2 mole of dithiocarbamate salt preferably at a temperature between 0° C. and 200° C. and a pressure of atmospheric to 100 psig for a period of 1 to 8 hours. The reaction product thus obtained is purified by filtering, washing and stripping and is then suitable for use as an additive in a lubricating oil. Although I do not wish to be bound by the following structural formula, the resulting product is thought to have the following structure:

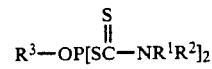

where $R^1$, $R^2$ and $R^3$ are as defined above.

The lubricant compositions hereof may comprise any oleaginous materials that require lubricative properties under extreme pressure conditions and require protection against deterioration by oxidation or by excessive wear under operating conditions. Specially suitable for use with the additives of this invention are liquid hydrocarbon oils of any suitable lubricating viscosity. In general, the lubricant compositions may comprise any mineral or synthetic oil of lubricating viscosity or mixtures thereof. The additives of this invention are especially useful in automotive engine oils, marine diesel oils, aviation lubricants, greases, and in automotive fluids such as brake fluids, power brake fluids, transmission fluids, power steering fluids, various hydraulic fluids and industrial gear oils and in liquid hydrocarbyl fuels.

In instances where synthetic oils are desired in preference to refined petroleum or mineral oil they may be employed alone or in combination with a mineral oil. They may also be used as the vehicle or base of grease compositions. Typical synthetic lubricants include polyisobutylene, polybutenes, hydrogenated polydecenes, polypropylene glycol, polyethylene glycol, trimethylol propane esters, neopentyl and pentaerythritol esters of carboxylic acids, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis(p-phenoxy phenyl) ether, phenoxy phenylethers, dialkylbenzenes, etc.

As hereinbefore indicated, the aforementioned additives can be incorporated as additives in grease compositions. When high temperature stability is not a requirement of the finished grease, mineral oils having a viscosity of at least 40 SSU at 150° F. are useful. Otherwise those falling within the range of from about 60 SSU to about 6,000 SSU at 100° F. may be employed. The lubricating compositions of the improved greases of the present invention, containing the above-described additives, are combined with a grease forming quantity of a thickening agent. For this purpose, a wide variety of materials can be dispersed in the lubricating oil in grease-forming qualities in such degree as to impart to the resulting grease composition the desired consistency. Exemplary of the thickening agents that may be employed in the grease formulation are metal soaps as well as non-soap thickeners, such as surface-modified clays and silicas, aryl ureas, calcium complexes and similar materials. In general, grease thickeners are employed which do not melt or dissolve when used at the required temperature within a particular environment; however, in all other respects, any material which is normally employed for thickening or gelling oleaginous fluids or forming greases may be used in the present invention.

Generally the lubricants and fuels of the present invention contain an amount of the product effective to improve extreme pressure properties and antiwear and oxidation characteristics. Normally this amount will be about 0.01–20%, preferably about 0.01–10%, of the total weight of the lubricant.

The invention also contemplates the use of other additives in combination with the additive of this invention. Such other additives include, for example, detergents and dispersants of the ash-producing or ashless type, corrosion-inhibiting agents, auxiliary oxidation-inhibiting agents, pour point depression agents, auxiliary extreme pressure agents, color stabilizers and anti-foam agents.

The following examples serve to illustrate the present invention, but are not intended as limitations thereon unless otherwise stated.

EXAMPLE 1

Preparation of Phosphorodichloridite

Phosphorus trichloride ($PCl_3$) 650 grams (an excess) was charged into a 2-liter reaction vessel under conditions avoiding contact with moisture. To the phosphorus trichloride there was slowly added 440 grams of nonylphenol in a non-reactive atmosphere (nitrogen) over a period of four hours. The exothermic reaction temperature was maintained between 55° and 60° C. After all of the nonyl phenol was added, the reaction mixture was stirred for an additional hour and the excess phosphorus trichloride was then removed by distillation, leaving behind the desired product, the nonylphenyl phosphorodichloridite, in a quantitative yield.

EXAMPLE 2

Preparation of Triethylammonium Dithiocarbamate Salt

The triethylammonium salt of N,N-di-2-ethylhexyldithiocarbamic acid was prepared by reacting di-2-ethylhexylamine and carbon disulfide in the presence of triethylamine in toluene. This is a reaction well known to those skilled in the art. To 0.5 moles of this salt there was added drop-wise 0.25 moles of the nonylphenyl phosphorodichloridite compound prepared in Example 1 dissolved in 250 milliliters of toluene. An exothermic reaction resulted. After the exothermic reaction had subsided, the reaction mixture was stirred and heated at 50° to 60° C. for six hours. It was then cooled and filtered. The filtrate was washed with water, dried over magnesium sulfate, and stripped of solvent. The yield was 210 grams (a 95% yield) of a clear light brown reaction product.

Similar products were prepared utilizing octyl alcohol, and octadecyl alcohol reacted with phosphorus trichloride and the intermediate product obtained reacted with the triethyl ammonium salt of N,N-di-2 ethylhexyl-, N,N-dibutyl- or N,N-didodecyl- dithiocarbamic acid.

EXAMPLE 3

Evaluation of Product

The additive prepared in Example 2 was blended in a concentration of 1% into a neutral base stock oil and tested for effectiveness as an antioxidant. The blend was further tested in a standard 4-Ball Test Machine for antiwear activity. Test results are shown in Tables 1 and 2. Table 3 shows results of the oxidation and corrosion test conducted of a proprietary blend, i.e., a blend containing in addition to the additive of this invention other commercial additives used in manufacturing a standard commercial lubricating oil.

The oxidation test reported in Tables 1 and 3 consists basically of bubbling a stream of air through a volume of the lubricant at the rate of about 5 liters per hour at 325° F. for 40 hours. Present in the composition are samples of metals commonly used in engine construction, namely iron, copper, aluminum and lead. See U.S. Pat. No. 3,682,980, incorporated herein by reference, for further details of the test. Reductions in viscosity index or neutralization number (or both) show effective control.

The Shell 4-ball wear test for scarring utilized S2100 stainless steel balls of ½ inch diameter under a 60 Kg load for 30 minutes; at 2000 r.p.m. at 200° F. and 300° F.

TABLE 1

| B-10 Catalytic Oxidation Test 325° F., 40 Hours, $R^3O-P[SC(=S)-NR^1R^2]_2$ | | |
|---|---|---|
| Item Additive (1%) | ΔNN | % ΔKV |
| 1 None | 17.6 | 142.8 |
| 2 $R^3 = C_9H_{19}-\text{Ph}$ ; $R^1 = R^2 = C_8H_{17}$ | 3.6 | 43.3 |
| 3 $R^3 = C_9H_{19}-\text{Ph}$ ; $R^1 = R^2 = C_4H_9$ | 2.4 | 47.5 |
| 4 $R^3 = C_8H_{17}$; $R^1 = R^2 = C_{12}H_{25}$ | 3.4 | 38.3 |
| 5 $R^3 = C_{18}H_{37}$; $R^1 = R^2 = C_8H_{17}$ | 2.4 | 40.9 |
| 6 $R^3 = C_{18}H_{36}$; $R^1 = R^2 = C_4H_9$ | 5.3 | 30.1 |

TABLE 2

4-Ball Wear Test, 2000 rpm
½" Balls, S2100 Steel, 60 kg, 30 Minutes $$R^3O-P(=S)[SC-NR^1R^2]_2$$

| Item | Additive (1%) | Wear Scar Diam (mm) 200° F. | 300° F. |
|---|---|---|---|
| 1 | None | 2.19 | 2.92 |
| 2 | $R^3 = C_9H_{19}$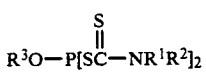; $R^1 = R^2 = C_8H_{17}$ | 0.53 | 0.63 |
| 3 | $R^3 = C_9H_{19}$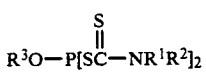; $R^1 = R^2 = C_4H_9$ | 0.54 | 0.63 |

TABLE 3

Oxidation and Corrosion Test
400° F., 72 Hours

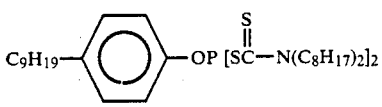

|  | Proprietary Blend 0% Additive | Proprietary Blend Plus 0.25% Additive Example 2 |
|---|---|---|
| Oxidation & Corrosion | | |
| % ΔKV @ 100° C. | 388 | 11.55 |
| % ΔNN | 12.2 | 1.21 |
| Metals, mg/cm | | |
| Al | 0 | 0.0 |
| Ag | −0.0003− | −0.0002 |
| Cu | −0.0125 | −0.0011 |
| Steel | −0.001 | 0.0 |
| Mg | −.2164 | 0.0 |
| Sludge | | |
| Vapor | Medium | Light |
| Interface | Heavy | Light |
| Liquid | Heavy | Nil |
| SAE Wear | Fail | Pass |
| 30 Days Storage Stability | | |
| 0° F. | | Pass |
| 70° F. | | Pass |

TABLE 3-continued

Oxidation and Corrosion Test
400° F., 72 Hours

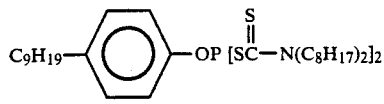

|  | Proprietary Blend 0% Additive | Proprietary Blend Plus 0.25% Additive Example 2 |
|---|---|---|
| 150° F. | | Pass |

I claim:

1. A method for preparing an additive for lubricating compositions comprising: reacting an amine or metal dithiocarbamate salt having the following structural formula:

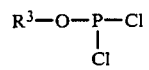

where $R^1$ and $R^2$ are the same or different and each is a hydrocarbyl group containing from 1 to 36 carbon atoms having none or at least one heteroatom which can be oxygen, sulfur or nitrogen and Y is an ammonium or metal radical, with an organo phosphorus dichloridite having the structural formula:

$$R^3-O-\underset{Cl}{P}-Cl$$

where $R^3$ is an aryl, alkaryl, aralkyl, or a saturated or unsaturated alkyl group, wherein the reactants are reacted in a molar ratio of 1 mole of the organo phosphorus dichlorodite compound to 2 moles of dithiocarbamate salt.

2. The method of claim 1 wherein the reactants are reacted at a temperature of about 0° C. to about 200° C. and at a pressure of about 0 psig to about 100 psig.

3. The method of claim 1, wherein $R^1$ and $R^2$ are selected from the group consisting of alkyl, alkenyl, aryl, aralkyl, and alkaryl radicals containing phenyl, naphthyl, or anthryl substituents.

4. The method of claim 1 wherein the dithiocarbamate salt is the triethylammonium salt of N,N-di-2-ethylhexyl-dithiocarbamic acid.

5. The method of claim 1 wherein the dithiocarbamate salt is the salt of a dithiocarbamic acid selected from the group consisting of N,N-dibutyldithiocarbamic acid and N,N-didodecyl-dithiocarbamic acid.

6. The method of claim 1 wherein the organo phosphorus dichlorodite is prepared by reacting a hydroxy-bearing compound selected from the group consisting of aryl, aralkyl, or alkaryl phenols, and saturated or unsaturated alkyl alcohols.

* * * * *